United States Patent [19]

Lee et al.

[11] Patent Number: 5,460,954

[45] Date of Patent: Oct. 24, 1995

[54] PRODUCTION OF HUMAN PROINSULIN USING A NOVEL VECTOR SYSTEM

[75] Inventors: Hyune W. Lee, Seoul, Rep. of Korea; Ji W. Yoon, Alberta, Canada; Yup Kang, Seoul, Rep. of Korea; Hyune S. Lee, Seoul, Rep. of Korea; Jae H. Lee, Seoul, Rep. of Korea; Choong S. Kim, Seoul, Rep. of Korea

[73] Assignee: Cheil Foods & Chemicals, Inc., Seoul, Rep. of Korea

[21] Appl. No.: 954,364

[22] Filed: Sep. 30, 1992

[30] Foreign Application Priority Data

Apr. 1, 1992 [KR] Rep. of Korea ......................... 92-5628
Jun. 25, 1992 [KR] Rep. of Korea ....................... 92-11138

[51] Int. Cl.$^6$ ............................ C12N 15/09; C12N 15/17
[52] U.S. Cl. ................ 435/69.5; 435/240.1; 435/252.33; 435/320.1; 536/23.1
[58] Field of Search ............................... 435/69.4, 240.1, 435/320.1, 252.33; 536/23.1

[56] References Cited

U.S. PATENT DOCUMENTS 5,017,478  5/1991  Cashion et al. ......................... 435/69.1
5,102,789  4/1992  Siegal et al. ..

OTHER PUBLICATIONS

Kang et al., 1991, Biotechnology Letters, 13, 755–760.
Goeddel et al., "Expression in *Escherichia coli* of Chemically Synthesized Genes for Human Insulin" *Proc. Natl. Acad. Sci. USA* 76(1):106–110 (1979).
Chance et al., "Chemical, Physical, and Biological Properties of Biosynthetic Human Insulin" *Diabetes Care* 4(2):147–154 (1981).
Williams et al., "Cytoplasmic Inclusion Bodies in *Escherichia coli* Producing Biosynthetic Human Insulin Proteins" *Science* 215:687–689 (1982).
Frank et al., "The Production of Human Proinsulin and its Transformation to Human Insulin and C–Peptide" In: *Peptide* (eds. Rich and Gross, Dierce Chemical Company, Rockford, Ill.) pp. 729–738 (1981).
Guo et al., "Synthesis of Human Insulin Gene" *Gene* 29:251–254 (1984).
Sung et al., "Short Synthetic Oligodeoxyribonucleotide Leader Sequences Enhance Acculation of Human Proinsulin Synthesized in *Escherichia coli*" *Proc. Natl. Acad. Sci. USA* 83:561–565 (1986).
Laemmli, U. K., "Cleavage of Structure Proteins during the Assembly of the Head of Bacteriophage T4" *Nature* 227:680–685 (1970).

*Primary Examiner*—Garnette D. Draper
*Assistant Examiner*—Sally Teng
*Attorney, Agent, or Firm*—Campbell and Flores

[57] ABSTRACT

The specification describes a process for producing human proinsulin in *Escherichia coli* (*E. coli*) using gene manipulation technology. The process can provide for human proinsulin in high yields by a novel expression vector having strong regulatory elements of an insulin gene and a stable recombinant gene product. The expression vector of the present invention is characterized in that: 1) it has an 11 amino acid leader peptide containing six threonines in order to ensure an intracellular stability of proinsulin fusion protein, 2) it contains two copies of a DNA expression cassette each comprising a strong lambda $P_R$ promoter, a lac ribosome binding site, a proinsulin gene with a 17 amino acid leader peptide sequence containing a DNA sequence encoding (Thr)$_6$, and a strong fd phage transcription terminator (combination of phage fd terminator and translation stop codon), etc. successively ligated, 3) it has an ampicillin resistance gene, 4) it can be very stably retained within a cultured cell, and 5) there are a number of these expression vectors in *E. coli* by which the expression can be significantly increased. Human insulin is prepared from the proinsulin fusion protein by in vitro conversion.

7 Claims, 5 Drawing Sheets

1 2 3 4 5 LM

TIME AFTER HEAT INDUCTION (hrs)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AATTCCACCA  CCACCACCAC  CACCAAATTC  CGT                                    33
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Thr  Thr  Thr  Thr  Thr  Thr
 1              5
```

PRODUCTION OF HUMAN PROINSULIN USING A NOVEL VECTOR SYSTEM

BACKGROUND OF THE INVENTION

1. Field of the Invention

The present invention relates to a process for producing human proinsulin in *Escherichia coli* (*E. coli*) using gene manipulation technology. More specifically, the present invention relates to a process for producing human proinsulin in a high yield by a novel expression vector having strong regulatory elements for the proinsulin gene and capable of producing a stable recombinant gene product.

2. Description of the Prior Art

The synthesis of human insulin using gene manipulation technology has been accomplished by one of the following two methods. In the first method, each gene of the alpha and beta chains of insulin is cloned and expressed. The proteins were purified followed by refolding them into insulin (Goeddel et al., (1979) *Proc. Natl. Acad. Sci. U.S.A.* 76: 106–110; Chance et al., (1981) *Diabetes Care*, 4:149–154). However, this method has serious defects because separate preparation of two chains imposes undue tasks to those skilled in the art, and reconstitution of the two chains results in a significant decrease in yields. In addition, the reconstitution procedures are very complicated.

The second method is a direct production of insulin which comprises cloning a gene encoding the alpha and beta chains fused with another protein gene in a plasmid to produce the proinsulin fusion protein in bacteria analogous to the process by which insulin is secreted in the pancreas (William et al., (1982) *Science*, 215:687–689; Frank et al., (1981) in *Peptides: Synthesis, Structure and Function; Proceedings of the Seventh American Peptide Symposium*, Rich, D. H. and Gross, E., eds., Pierce Chemical Co., Rockford, Ill., pp. 729–738). This method is useful since it requires a single fermentation and a simple isolation procedure to obtain the proinsulin. In addition, the proinsulin can be refolded into tertiary structure more efficiently as compared to the first method.

However, since the yield of foreign protein such as proinsulin in intracellular expression in *E. coli* by gene manipulation technology is inversely proportional to the size of the expressed fused peptide, the insertion of a huge size of fused peptide gene into the recombinant expression vector of the proinsulin gene is undesirable. Thus, in order to insure stability of proinsulin in *E. coli* and simplify the purification procedure, there is a need to design a fused gene in which both facts are taken into consideration. Over the past decade, the present inventors and other research groups have attempted to reduce the size of the fused peptide by removing the β-galactosidase portion (Guo et al., (1984) *Gene* 9:251–255; Yoon et al., (1988) In: Recombinant DNA Techniques, J. W. Yoon, editor, KOSCO Inc. Seoul, pp. 93–115), or replacing this peptide with a short fused peptide (Sung et al., (1986) *Proc. Natl. Acad. Sci. U.S.A.* 83:561–565). In addition, an attempt to maintain intracellular stability in *E. coli* of proinsulin expressed by combination of multiple proinsulin genes has been made, and *E. coli* which is deficient in a specific cellular protease has been used as a host to protect the intracellular degradation of proinsulin.

As a result, minor improvements have been made, but many limitations still exist, including a) problems in reducing the size of gene to be fused; b) long expression time; c) difficulties in exact refolding of the modified proinsulin in vitro; and d) low yields.

In order to eliminate and minimize these drawbacks, the present inventors have constructed a new recombinant expression vector to produce proinsulin (pYK10-9). The inventors have found that it is possible to prevent the expressed proinsulin from being degraded in the cell and to escape from the target of protease by attaching an oligonucleotide (SEQ ID NO. 1) containing a gene encoding (Thr)$_6$ (SEQ ID NO. 2) to the 5'-end of the proinsulin gene, and efficiently control the expression of the fused proinsulin by using a novel plasmid into which a strong promoter (lambda P$_R$) in combination with a proinsulin fusion protein gene containing a lac ribosome binding site are inserted.

However, although it was possible to increase the intracellular stability of proinsulin fusion protein by decreasing the size of the fused peptide, some problems still remain in producing insulin products on a large scale. That is, the administration amount of insulin currently used as a diabetic treating agent is considerably large, being 40 mg per dose. In addition, once the insulin is injected, it should be permanently administered. Therefore, the expression utilizing *E. coli* should be significantly enhanced because of the difficulty in the purification procedure.

Various methods, for example, using a strong promoter such as lambda P$_R$ promoter which the present inventors have used, using a synthetic promoter such as tac promoter, or inserting two or more genes under the control of single promoter, and the like, have been proposed to improve the expression.

However, the use of a single promoter has some limitations. Thus, a case wherein a plurality of genes are successively inserted under the control of a single promoter may be taken into consideration, but it is also difficult to use this alternative due to the following problems. First, when multiple structural genes are successively arranged under the single promoter, multimers to which a single protein is one dimensionally bound are produced. Thus, in order to make the protein to be an active monomer, an additional treatment, such as CNBr cleavage, should be carried out. However, this treatment is not so realizable in view of the fact that the reaction site of CNBr is methionine. Second, since a protein having a relatively large molecular weight is synthesized as compared with the monomer, substantial improvements in the expression cannot be expected. Furthermore, as with most critical problems, it has been found that physical control of gene expression, which is the fundamental requirement for gene expression as well as the development of industrial strains is impossible due to the absence of effective transcriptional and translational control means when each gene is expressed.

Therefore, to solve these problems, the present inventors have constructed a new recombinant expression vector to produce proinsulin (pYD21). As a result, the present inventors have found that it is possible to produce human proinsulin on an industrial scale by inserting two or more copies of a DNA expression cassette each comprising a lambda P$_R$ promoter, a proinsulin fusion protein gene, a lac ribosome binding site, and a phage fd transcription terminator into a single plasmid.

SUMMARY OF THE INVENTION

Accordingly, it is an object of the present invention to provide a process for producing human proinsulin in a high yield using a novel vector system.

It is another object of the present invention to provide an expression vector capable of producing human proinsulin with enhanced expression and in a high yield. This vector contains two or more copies of a DNA expression cassette each comprising a lambda $P_R$ promoter, a lac ribosome binding site, the proinsulin fusion protein gene, and a phage fd transcription terminator.

It is a further object of the present invention to provide a microorganism transformed with a new expression vector capable of producing human proinsulin.

These and other objects of the present invention can be achieved by a process for producing human proinsulin in *E. coli* on a large scale which comprises the steps of:

a) inserting a DNA sequence comprising a lac ribosome binding site, a DNA encoding an 11 amino acid leader peptide sequence containing a DNA sequence encoding $(Thr)_6$, and human proinsulin, into a plasmid consisting of a lambda $P_R$ promoter and a fd phage transcription terminator to construct an expression vector, wherein said cDNA encoding human proinsulin is inserted between said DNA encoding an 11 amino acid leader peptide sequence and said fd phage transcription terminator;

b) isolating a DNA expression cassette comprising, in turn, a lambda $P_R$ promoter, a lac ribosome binding site, a DNA encoding an 11 amino acid leader peptide sequence containing $(Thr)_6$, a cDNA encoding human proinsulin, and a fd phage transcription terminator from said expression vector constructed in Step a);

c) reinserting said DNA expression cassette isolated from Step b) into another vector constructed in Step a) so that the two expression cassettes are transcribed in opposite directions, resulting in an expression vector having two copies of DNA expression cassettes;

d) transforming *E. coli* with said expression vector having two copies of DNA expression cassettes obtained in Step c) to produce a transformant;

e) culturing said transformant in an appropriate medium; and f) recovering said human proinsulin fusion protein.

BRIEF DESCRIPTION OF THE DRAWINGS

The present application will be hereinafter described in detail with reference to the accompanying drawings, wherein.

DETAILED DESCRIPTION OF THE INVENTION

The present invention provides a process for producing human proinsulin in a high yield using a novel vector system.

In order to produce a proinsulin product in a high yield, the present inventors have constructed a novel expression vector (pYD21) by inserting two copies of a DNA expression cassette each comprising a lambda $P_R$ promoter, a lac ribosome binding site, a proinsulin fusion protein gene, and a phage fd transcription terminator into a plasmid.

The genes encoding proinsulin fusion protein in the vector pYD21 are expressed and regulated by each of the expression cassettes; whereby the above mentioned disadvantages of the prior art can be overcome. That is, since proinsulin fusion protein is produced without forming a multimer in which a number of proinsulin fusion proteins are consecutively bound, cleavage procedures, such as a CNBr method, to cleave the multimer into respective monomers are not required. Furthermore, since a number of individual strong lambda $P_R$ promoters are acting, the expression of proinsulin can be increased.

The expression vector pYD21 of the present invention is characterized in that: 1) it has a precursor containing an 11 amino acid leader sequence containing six threonine residues in order to ensure an intracellular stability of proinsulin fusion protein, 2) it contains two copies of a DNA expression cassette each comprising a strong lambda $P_R$ promoter, a lac ribosome binding site, a cDNA encoding human proinsulin, and a strong terminator (a combination of phage fd terminator and translation stop codon), etc. successively ligated, 3) it has an ampicillin resistance gene, 4) it can be very stably remained within a cultured cell, and 5) it has a number of copies by which the expression can be significantly increased.

Accordingly, the present invention provides the expression vector pYD21 which can significantly increase the expression of proinsulin fusion protein. In addition, the present invention provides a process for producing human proinsulin fusion protein in a high yield which comprises the steps of transforming *E. coli* pop2136 with the vector pYD21 to obtain a transformant, culturing the transformant, and recovering the proinsulin from the cultured medium.

Figure 1:
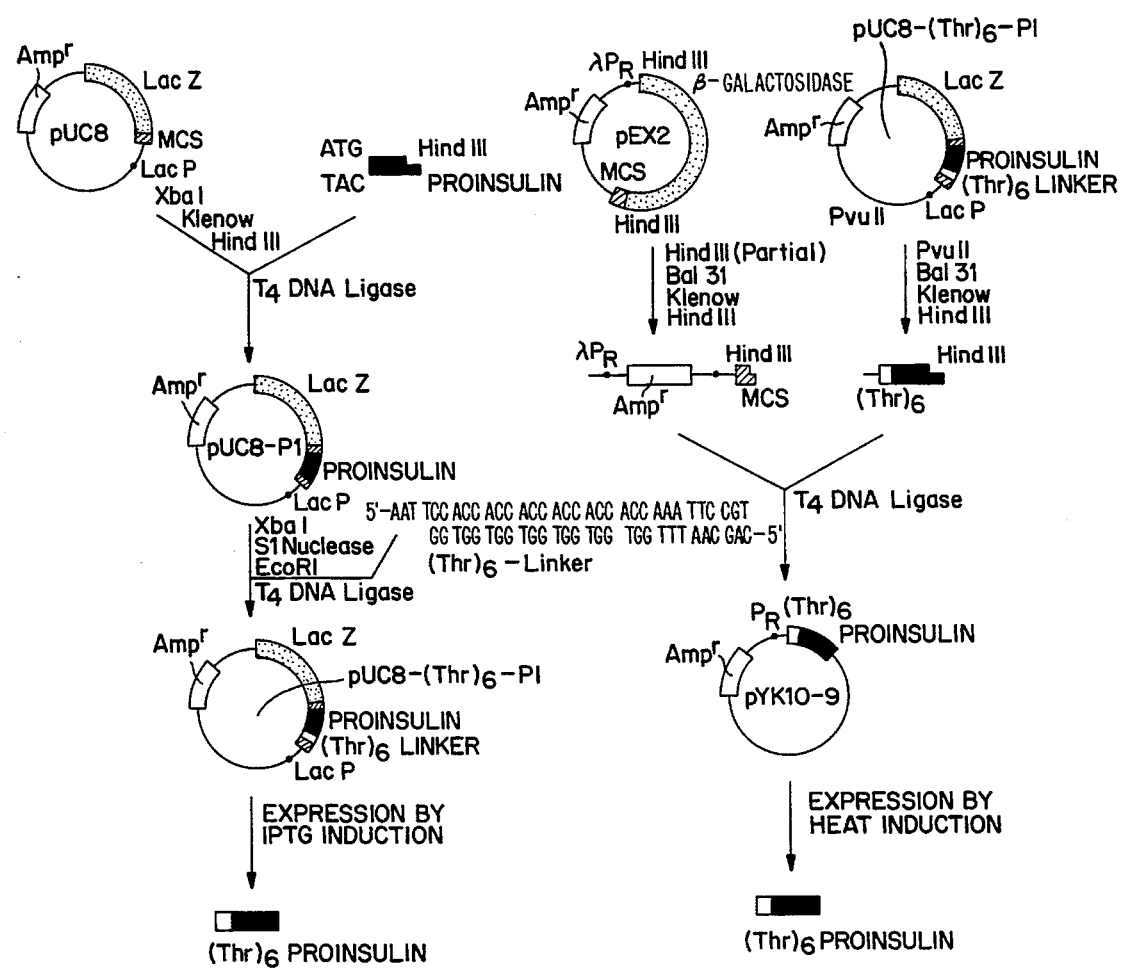
FIG. 1 is a schematic diagram showing the construction of human proinsulin expression vectors pUC8-$(Thr)_6$-PI and pYK10-9, wherein the hatched box indicates multicloning site (MCS); the black box: a proinsulin gene and product; the dotted box a β-galactosidase gene and product; and the white box a gene of threonine oligomer itself, and wherein $Amp^r$ represents a gene of ampicillin resistance; lambda $P_R$: a lambda phage $P_R$ promoter and lac P: a lac operon promoter (The size of the proinsulin fusion protein is shown relative to the size of the expressed fusion protein.)
Figure 2:
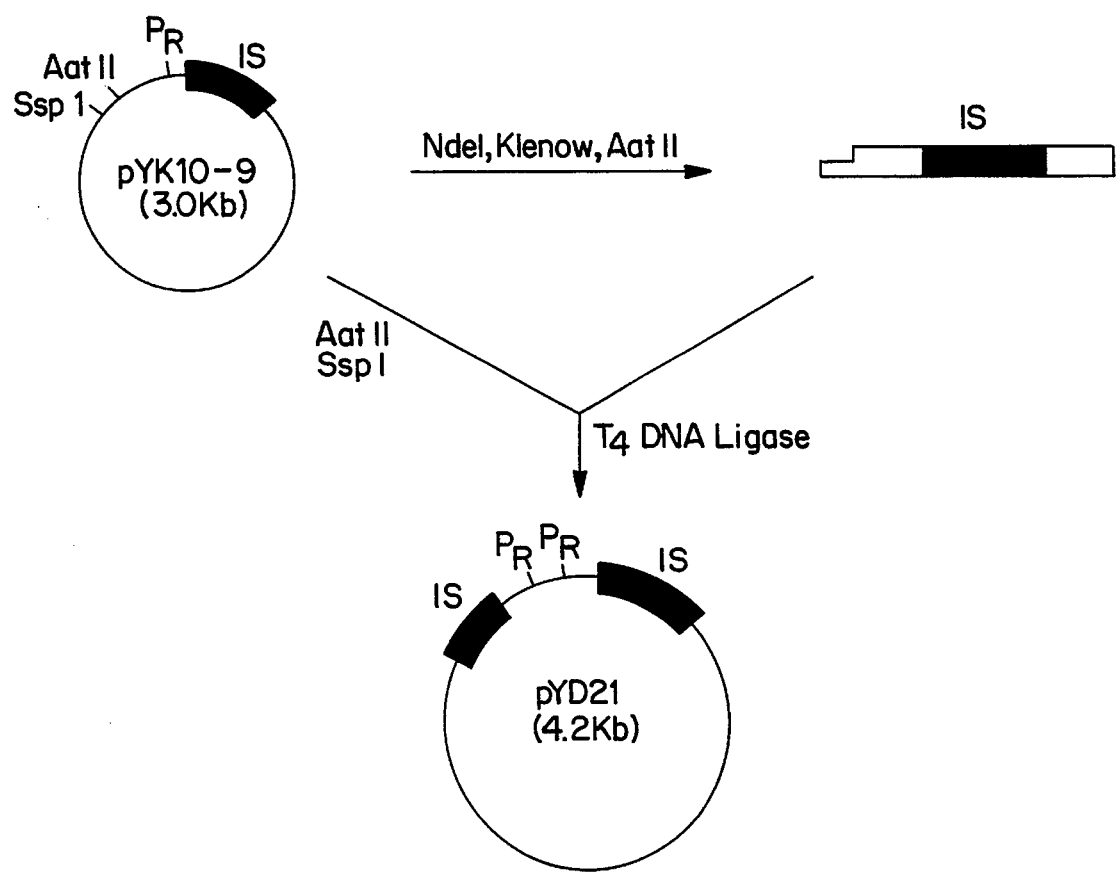
FIG. 2 shows a schematic diagram showing the construction of a human proinsulin expression vector pYD21 of the present invention.

In producing the proinsulin in *E. coli* according to the present invention, recombinant vectors were constructed as set forth below (see FIGS. 1 and 2).

Construction of pUC8-$(Thr)_6$-PI

As illustrated in FIG. 1A, the pUC8-$(Thr)_6$-PI expression vector was constructed by inserting the proinsulin gene [isolated from Langerhans' Islets in the human pancreas which was obtained from the Division of Transplantation Surgery (Foothills Hospital, University of Calgary, Alberta)] and a short oligopeptide gene into pUC8 plasmid (purchased from Gibco/BRL). The proinsulin gene containing a blunt initiation codon and a 3'-protruding Hind III end was subcloned in pUC8 by treatment with XbaI, Klenow polymerase, and Hind III. The recombinant pUC8-PI plasmid was linearized with EcoRI and annealed with a [Thr]$_6$ oligopeptide gene. The correctly constructed pUC8-(Thr)$_6$-PI vector was confirmed by a direct dideoxy DNA sequencing method.

Construction of pYK10-9

As shown in FIG. 1B, the pYK10-9 expression vector system is comprised of the lambda P$_R$ promoter bound to plasmid pEX2 (obtained from Boehringer Mannheim), and human proinsulin fusion protein gene containing the lac ribosome binding site with the (Thr)$_6$ gene. The expression vector pEX2 was partially cut with Hind III, digested further with Bal 31, and then completely cut with Hind III to obtain a lambda P$_R$ promoter. The proinsulin fusion protein gene, together with an oligonucleotide containing a lac ribosome binding site and the (Thr)$_6$ gene, was obtained from pUC8-(Thr)$_6$-PI by cutting it with Pvu II, sequentially digesting the lac Z gene with Bal 31, and finally, cutting it with Hind III. The lambda P$_R$ promoter was added to the 5'-end of the lac ribosome binding site and the (Thr)$_6$ gene. Various sizes of pYK expression vectors were obtained from random combinations of the lambda P$_R$ promoter and the lac ribosome binding sites. The best clone, that expressed the highest amount of proinsulin, was selected under 42° C. incubation according to the thickness of the band on SDS-PAGE gel and by C-peptide radioimmunoassay, and was designated pYK10-9. This plasmid was deposited on Mar. 16, 1992 in the Korean Culture Center of Microorganisms, Sodaemun gu, Seoul 120-749, Republic of Korea which is one of the international depositories recognized under the Budapest Treaty and received a deposit number KCCM 10015. This deposit was made in accordance with all of the requirements of the Budapest Treaty.

Construction of pYD21

The expression vector pYD21 was derived from the vector pYK10-9. The vector pYK10-9 was digested with SspI and precipitated with ethanol. After digesting the vector with Aat II, a 2.9 kb fragment was recovered by agarose gel electrophoresis. On the other hand, the expression vector pYK10-9 was digested with NdeI, treated with T4 DNA polymerase to make a blunt end, and then digested again with AatII to obtain a 1.2 kb fragment. These two fragments were ligated with T4 DNA ligase and used to transform *E. coli*. This vector has two copies of a DNA expression cassette each comprising an independent lambda P$_R$ promoter, a lac ribosome binding site, a proinsulin fusion protein gene, a fd phage transcription terminator, etc. in one backbone.

Host Cell

The bacterial strains used in the present invention were *E. coli* JM103 (obtained from Pharmacia) and *E. coli* pop2136 (obtained from Institut Pasteur, France). *E. coli* pop2136 has a CI857 repressor in chromosomes so that the lambda P$_R$ promoter can be regulated.

Gene Expression

The expression of fusion protein in accordance with the present invention was carried out by culturing *E. coli* pop2136 transformed with pYK10-9 and pYD21 in a 2xYT medium (1.6% tryptone, 1% yeast extract, 0.5% NaCl, pH 7.0) supplemented with 50 mg of ampicillin and 1 g of glucose per liter culture medium at 32° C. until the optical density (OD) of the culture medium reached 1.0 at 580 nm, and transferring the cultures to a 42° C. water bath.

The fermentation medium for fed-batch fermentation of *E. coli* pop2136/pYK10-9 and *E. coli* pop2136/pYD21 and the medium containing a growth limiting substrate are set forth in Tables 1 and 2 below. Dissolved oxygen was also adjusted at 20% of air saturation. Temperature was shifted from 32° C. to 42° C. A fresh medium as shown in Table 3 below was added to induce gene expression.

TABLE 1

Medium for Fed-batch Fermentation of *E. coli* pop2136/pYK10-9 and *E. coli* pop2136/pYD21

| Ingredient | g/l |
| --- | --- |
| Glucose | 5 |
| K$_2$HPO$_4$ | 6 |
| KH$_2$PO$_4$ | 3 |
| NaCl | 2 |
| (NH$_4$)$_2$SO$_4$ | 1.2 |
| MgSO$_4$ | 0.6 |
| ampicillin | 0.1 |

TABLE 2

Growth-limiting Substrate

| Ingredient | g/l |
| --- | --- |
| Glucose | 400 |
| (NH$_4$)$_2$SO$_4$ | 107 |
| MgSO$_4$.7H$_2$O | 8.5 |
| FeSO$_4$.7H$_2$O | 0.2 |
| CaCl$_2$.6H$_2$O | 0.08 |
| MnSO$_4$.5H$_2$O | 0.05 |
| ZnSO$_4$.7H$_2$O | 0.05 |
| CoCl$_2$.6H$_2$O | 0.01 |

TABLE 3

Medium to be Added after Expression by Heat Induction

| Ingredient | g/l |
| --- | --- |
| K$_2$HPO$_4$ | 4.4 |
| Yeast extract | 2.0 |

Assay Protocol

The amounts of proinsulin expressed were measured by C-peptide radioimmunoassay. Recombinant *E. coli* cells were harvested by centrifugation at 3000 rpm for 5 minutes, dissolved in phosphate buffered saline (PBS, pH 7.8), and disrupted by sonication. The sonicated cells were precipitated by placing them in a cold room for 30 minutes. The precipitated fusion protein was collected by centrifugation (12,000 rpm for 5 minutes), redissolved in 6M guanidinium-HCl, and then diluted with PBS (500-fold). The concentration of proinsulin in the diluted sample solution was measured by C-peptide radioimmunoassay according to the supplier's manual (Daichi Radioisotope Lab, Tokyo, Japan) [Yoon, J. W., Lesniak, M. A., Fussganger, R. and Notkins, A. L. (1976) *Nature* 264:178–180].

The amounts of proinsulin fusion protein were measured by SDS-PAGE. SDS-PAGE was carried out as described elsewhere [Laemmli, U.K. (1970) *Nature* 227:680–685]. A 15% polyacrylamide gel was used for analysis of the proteins from the expression vectors pYK10-9 and pYD21. The loading samples were prepared by dissolving the harvested cells in a loading buffer (5% SDS, 73 mM Tris, pH 6.8, 10 mM DTT) and followed by denaturation with heating (95° C. for 2 minutes).

DESCRIPTION OF THE PREFERRED EMBODIMENT

The present invention will be illustrated in greater detail by means of the following non-limiting examples.

EXAMPLE 1

Cloning of Human Proinsulin by a cDNA Cloning Method

Langerhans' Islets in the human pancreas was isolated, and homogenized using a Polytron mixer followed by addition of 5 g/ml of 4M guanidine-isothiocyanate solution. Then, chromosomal DNA was destroyed with an 18 gauge syringe. From the mixture, protein was removed by extraction with a large amount of phenol/chloroform solution preheated to 60° C. This treatment was repeated several times, subsequently treating with proteinase K. This solution from which protein was removed was precipitated with ethanol to give total RNA. An oligo d(T)-cellulose column chromatography was used to isolate a mRNA having Poly(A) at 3'-end from the total RNA. Synthesis of single-stranded cDNA from the isolated poly(A)-mRNA was carried out by annealing an oligo d(T) primer followed by reverse transcription for 40 minutes at 42° C. To the single-stranded cDNA reaction solution (cDNA/mRNA hybrid), E. coli ribonuclease H was added so as to digest mRNA, and then E. coli DNA polymerase I was added so as to synthesize the double-stranded cDNA. The 3'-end of the double-stranded cDNA synthesized was removed by T4 DNA polymerase and hair-pin loop at 5'-end was removed by S1 nuclease. The double stranded cDNA was reacted with TdT (Terminal deoxynucleotidyl Transferase) to prepare C-tailed cDNA. Meanwhile, pBR322 was used as a cloning vector. First, pBR322 vector was cut with Pst I, and reacted with TdT to prepare G-tailed linear pBR322. The C-tailed cDNA and G-tailed pBR322 were ligated with T4 DNA ligase, and used to transform E. coli. The ligation mixture was plated on the medium containing 2x YT+50 µg/ml of tetracycline to obtain tetracycline resistant transformants. A colony having a plasmid containing a preproinsulin gene was obtained from these transformants using a colony hybridization method. The preproinsulin gene was isolated from the plasmid, and subcloned into pTZ18R vector (purchased from Amersham) to prepare pTZ18-HI vector. DNA sequences of the insulin gene was confirmed by a dideoxy chain-termination method.

pTZ18-PI containing a single proinsulin gene was prepared from the above pTZ18-HI which contained the preproinsulin gene by a site-specific gene trimming method. First, a reverse primer was attached to the single-stranded DNA of pTZ18-HI, and a partially double-stranded DNA was prepared using Klenow polymerase I. The plasmid was digested with EcoR I, and a linear single-stranded pTZ18-HI was isolated using alkaline gel electrophoresis. After a synthetic primer having an initiation codon (ATG) was attached to the DNA, and 5'→3' synthesis and 3'→5' elimination were carried out with the Klenow polymerase I, a proinsulin gene having a 5'-blunt end and a 3'-end of Hind III was isolated by cutting with Hind III. After cutting with BamH I and making a blunt end with Klenow polymerase, a pTZ18-PI vector having only a proinsulin gene was constructed by inserting the isolated proinsulin gene into the pTZ18R vector cut with Hind III. This pTZ18-PI vector was used to construct an expression vector pUC8-(Thr)$_6$-PI.

EXAMPLE 2

Recombination of Expression Vector pUC8-(Thr)$_6$-PI

This example is illustrated with reference to FIG. 1A.

The pUC8 plasmid (purchased from Gibco/BRL) was cut with Xba I (buffer solution: 10 mM Tris-HCl, 10 mM MgCl$_2$, 50 mM NaCl, 1 mM DTT, 5 µM BSA, pH 7.9), and a 3'-Xba I end was converted to a 3'-blunt end with Klenow polymerase. The DNA was ethanol precipitated, dissolved into Hind III buffer solution (10 mM Tris-HCl, 10 mM MgCl$_2$, 50 mM NaCl, 1 mM DTT, pH 7.9), and cut with Hind III. This DNA was treated with BAP (bacterial alkaline phosphatase), and then a large DNA fragment was recovered and purified from 0.8% agarose gel electrophoresis. The pTZ18-PI plasmid was treated with EcoR I and Bal 31, and then with Sau 3A I (buffer solution: 10 mM Bis Tris Propane, 10 mM MgCl$_2$, 1 mM DTT, 50 µM BSA, pH 7.0), S1 nuclease (buffer solution: 30 mM sodium acetate, 50 mM NaCl, 1 mM zinc acetate, 0.5 mg/ml heat denatured DNA, pH 4.6), and Hind III in order to isolate and purify a proinsulin gene. The two fragments purified above were ligated with T4 DNA ligase, and the ligation mixture was used to transform E. coli JM103 (purchased from Pharmacia). In the plasmids isolated from the transformed E. coli, pUC8-PI plasmid having a Xba I cutting site was obtained. The pUC8-PI was treated with Xba I, S1 nuclease, EcoR I, BAP, and the like, and a large segment was isolated in order to insert a DNA fragment containing the proinsulin gene of the pUC8-PI.

The DNA fragment containing a gene encoding (Thr)$_6$ was chemically synthesized and treated with T4 polynucleotide kinase (buffer solution: 70 mM Tris-HCl, 10 mM MgCl$_2$, 0.1 mM spermidine, 5 mM DTT, 0.1 mM EDTA, 60 µM ATP, pH 7.6). The large segment of pUC8-PI isolated and the DNA fragment containing a gene encoding (Thr)$_6$ were ligated, and the ligated DNA was used to transform E. coli JM103 to obtain an expression vector pUC8-(Thr)$_6$-PI. The (Thr)$_6$-PI portion of pUC8-(Thr)$_6$-PI was inserted into pTZ18R to obtain a pTZ18-(Thr)$_6$-PI plasmid, which was identified for the DNA sequence of proinsulin.

EXAMPLE 3

Recombination of Expression Vector pYK Series

This example is illustrated with reference to FIG. 1B.

The pEX2 vector (obtained from Boehringer Mannheim) was partially digested with Hind III, ethanol precipitated, and dissolved in a Bal 31 buffer solution (600 mM NaCl, 12 mM CaCl$_2$, 12 mM MgCl$_2$, 20 mM Tris-HCl, 1 mM EDTA, pH 8.0), and then treated with Bal 31 at 30° C. for various time periods. After the Bal 31 treated DNA was ethanol precipitated and dissolved in a Hind III buffer solution to completely cut with Hind III, the linear DNA having a lambda P$_R$ promoter was purified by 0.8% agarose gel electrophoresis. A proinsulin gene containing a gene encoding (Thr)$_6$ was isolated by treating pTZ18-PI plasmid with Pvu II (buffer solution: 50 mM Tris-HCl, 10 mM MgCl$_2$, 10 mM NaCl, 1 µM DTT, pH 7.9) and Bal 31, and then digesting it with Hind III. Various sizes of pYK expression vector series were constructed by ligating a gene having a lac ribosome binding site with 5'-end of the (Thr)$_6$-PI gene, and inserting the ligated DNA into the 3'-end of P$_R$ promoter. *E. coli* pop 2136 (obtained from Institut Pasteur, France) was transformed with the above vectors and the best clone, that expressed the highest amount of proinsulin fusion protein was selected by SDS-PAGE and C-peptide radioimmunoassay, and was designated pYK10-9.

EXAMPLE 4

Recombination of Expression Vector pYD21

This example is illustrated with reference to FIG. 2.

The expression vector pYK10-9 containing the human proinsulin gene was cut with a restriction enzyme Ssp I (buffer solution: 50 mM Tris-HCl, 10 mM MgCl$_2$, 100 mM NaCl, 1 mM DTT, pH 7.9) and ethanol precipitated. After the DNA was dissolved in Aat II buffer solution (10 mM Tris-HCl, 10 mM MgCl$_2$, 50 mM KCl, 1 mM DTT, pH 7.5) to cut it with Aat II, a 2.9 kb DNA fragment was purified from 0.8% agarose gel electrophoresis.

On the other hand, the expression vector pYK10-9 was cut with restriction enzyme Nde I (buffer solution: 50 mM Tris-HCl, 10 mM MgCl$_2$, 100 mM NaCl, 1 mM DTT, pH 7.9) and was made to blunt end through T4 DNA polymerase reaction. The DNA was digested with Aat II, and an about 1.2 kb DNA fragment containing a P$_R$ promoter, a lac ribosome binding site, a proinsulin gene, and a terminator was separated and isolated by electroelution from 0.8% agarose gel electrophoresis.

The 2.9 kb DNA and the 1.2 kb DNA were ligated using T4 DNA ligase (buffer solution: 100 mM Tris-HCl, 100 mM MgCl$_2$, 0.5 mM ATP, pH 7.6) and the ligate was used to transform *E. coli*.

EXAMPLE 5

Figure 3:
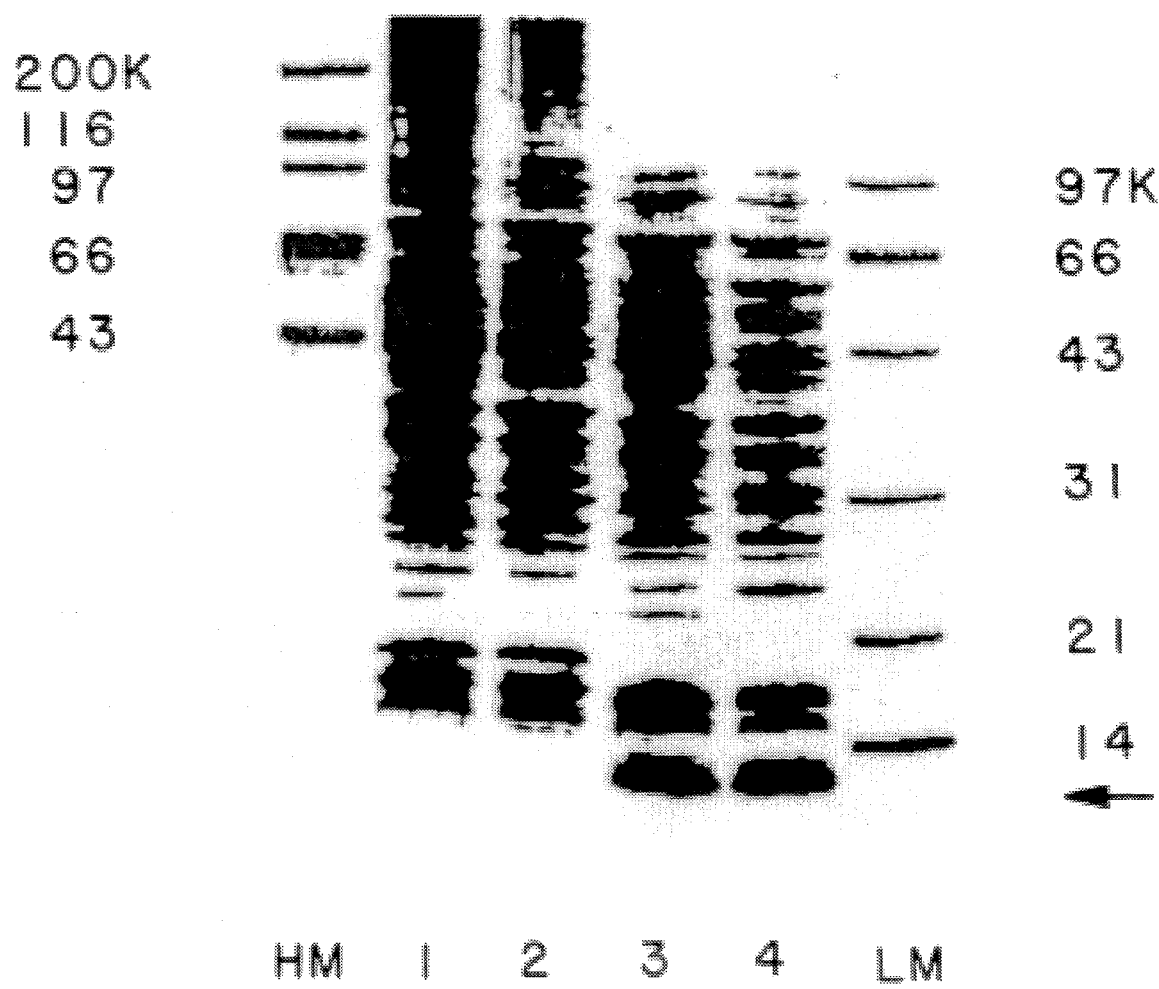
FIG. 3 is a SDS-PAGE photograph of a protein produced from the recombinant *E. coli* wherein a gene encoding human proinsulin is introduced, wherein Lane 1: *E. coli* JM103; Lane 2: *E. coli* pop2136; Lane 3: *E. coli* pop2136 containing pUC8-PI; Lane 4: *E. coli* pop2136 containing pYK10-9; H. M. and L. M.: high molecular weight standard and low molecular weight standard, respectively; and Lower arrow denotes 11.7 kilodalton proinsulin fusion protein containing $(Thr)_6$ peptide (Lane 3 and 4)

Expression of Proinsulin fusion Protein with pUC8-(Thr)$_6$-PI and pYK10-9 Vectors In order to confirm the expression of proinsulin fusion protein from the three cloned vectors, SDS-PAGE or C-peptide radioimmunoassay was used after the expression was induced. First, *E. coli* JM103/pUC8-(Thr)$_6$-PI was grown in a 2xYT medium containing 1 g/l of glucose and 50 mg/l of ampicillin. IPTG was added to the culture medium to a final concentration of 1 mM at 37° C. in order to induce the expression of the fusion protein. *E. coli* pop 2136/pYK10-9 was also cultured in the same medium. Cells were grown at 32° C. until the optical density (OD) of the culture medium reached 1.0 at A 580. At this time, the temperature of the cultures was shifted to 42° C. in order to induce the expression of the fusion protein by lambda P$_R$ promoter. From the expressed colonies, the amount of the proinsulin fusion protein was evaluated by SDS-PAGE (FIG. 3). The amount of the proinsulin in the fusion protein was determined by C-peptide radioimmunoassay.

The optimum expression time of the first vector pUC8-(Thr)$_6$-PI was 24 hours, and the expression ratio was approximately 20%. The total amount of the proinsulin produced per liter was 149 mg. In the second vector, pKY10-9, the optimum expression time was 8 hours which was shorter than that of the pUC8-(Thr)$_6$-PI vector. Furthermore, it was found that *E. coli* having pYK10-9 could grow in spite of the accumulation of expressed protein. Although the expression ratio of pYK10-9 was approximately 20% which was similar to that of pUC8-(Thr)$_6$-PI, the total amount of proinsulin was 249 mg/liter which was higher than that of pUC8-(Thr)$_6$-PI. The properties of these vectors are summarized in Table 4 below.

TABLE 4

| Properties of Proinsulin Expression Vectors | | |
|---|---|---|
| Vector | pUC8-(Thr)$_6$-PI | pYK10-9 |
| Promoter | lac | P$_R$ |
| Ribosome binding site | lac | lac |
| Induction | IPTG | Heat (42 C.) |
| Molecular weight of fusion protein | 12,000 | 12,000 |
| Total cell weight (g/l) | 10 | 15 |
| Expression ratio (%)* | 20 | 20 |
| Total amount of proinsulin (mg/l) | 149 | 249 |
| Expression time (hrs) | 24 | 8 |

Note)
*: Expression ratio (%) = [Fusion protein(Inclusion body)/Total protein] × 100

EXAMPLE 6

Expression of Expression Vector pYD21

Figure 5:
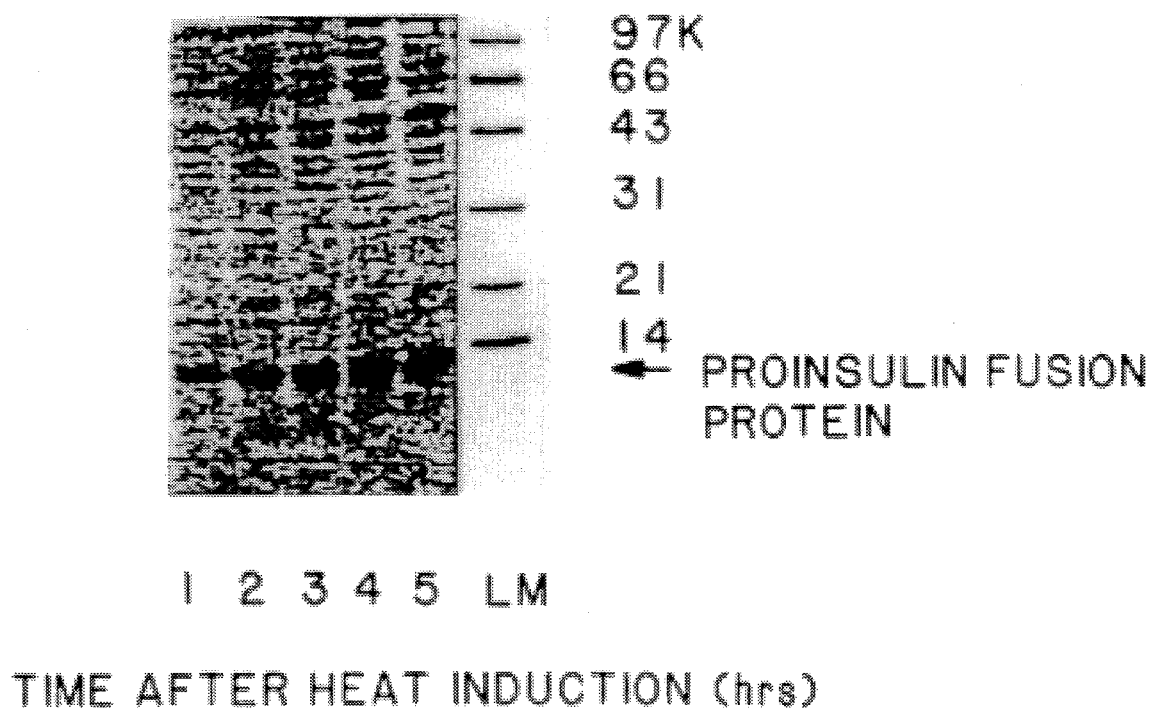
FIG. 5 is a photograph of proinsulin fusion protein production on time passed after *E. coli* pop2136 harboring the plasmid pYD21 was heat induced.

The recombinant expression vector pYD21 was expressed by a batch fermentation. At first, recombinant *E. coli* was inoculated into a 500 ml flask containing 500 ml of a seed culture (2xYT+glucose+ampicillin) and grown at 34° C. for 13 hours. 20 ml of the seed culture was inoculated into a 2.5 l fermentor containing 1 liter of a 2xYT+glucose+ampicillin medium, and cultured at 34° C. under aeration of 0.5 liter per minute, at 400 rpm, pH 6.8. After the cells were grown until OD reached 4–5 at 580 nm, the temperature of the fermentor was shifted to 42° C. to induce the expression. The amount of the proinsulin fusion protein was determined by SDS-PAGE and C-peptide radioimmunoassay (FIG. 5).

The expression ratio of pYK10-9 having a single DNA expression cassette was approximately 20% and the amount of proinsulin produced was 249 mg/l while the expression ratio of pYD21 having double DNA expression cassettes was about 28% and the amount of proinsulin was 328 mg/l which was significantly greater than that obtained with the pYK10-9 vector. Furthermore, the expression time for fusion protein was reduced. A comparison of the expressions between pYK10-9 and pYD21 is shown in Table 5 below.

TABLE 5

| Properties of Proinsulin Expression Vectors | | |
|---|---|---|
| Vector | pYK10-9 | pYD21 |
| Promoter | single P$_R$ | double P$_R$ |
| Ribosome binding site | single lac | double lac |
| Terminator | single phage fd terminator and stop codon | double phage fd terminator and stop codon |
| Total cell weight (g/l)*[1] | 15 | 15 |
| Expression ratio (%)*[2] | 20 | 28 |
| Total proinsulin (mg/l) | 249 | 328 |
| Expression time (hrs) | 8 | 7 |

*[1]: Total cell weight = Dry cell weight
*[2]: Expression ratio (%) = [Total amount of fusion protein/total amount of protein] × 100

EXAMPLE 7

Comparison of Expression for Fusion Proteins by Fed-batch Fermentation of Transformants with Expression Vectors pYK10-9 and pYD21

Fed-batch fermentation is characterized by starting with batch fermentation in a growth medium at an early stage, adding growth limiting substrates by means of predetermining the value of cell growth and mass balance to be modified when the concentration of the growth limiting substrates reaches zero, and controlling the concentration of dissolved oxygen to be above 20% of air saturation.

Figure 4:
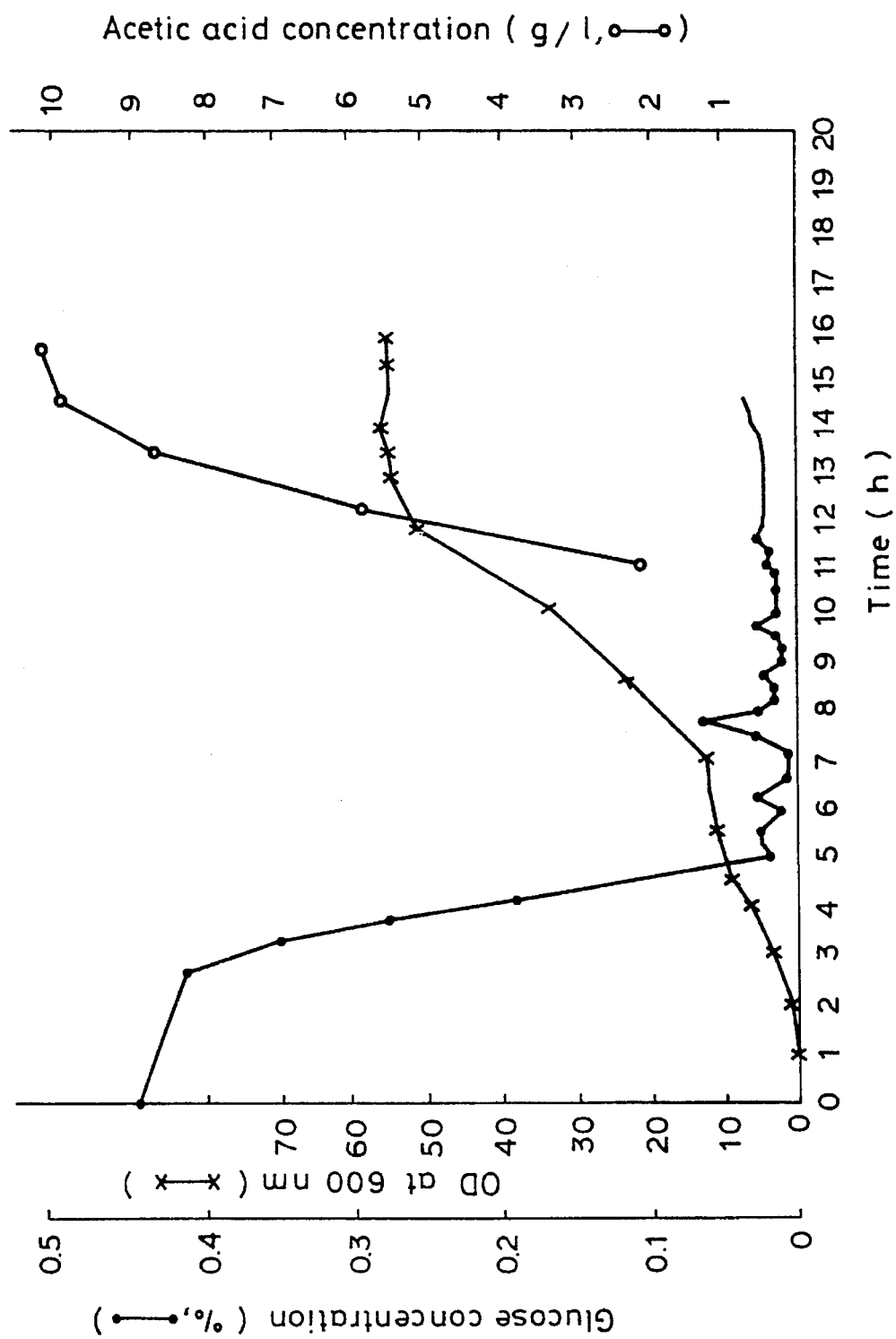
FIG. 4 is a graphical representation of fed-batch fermentation of *E. coli* pop2136 transformed with expression vector pYD21.

Primary seeds were cultured in a 15 ml tube containing 2 ml of a seed medium (2xYT+glucose+ampicillin) at 34° C. for 6 hours, and secondary seeds were cultured at 34° C. for 13 hours in a 1 liter flask containing 100 ml of the seed medium. 40 ml of the secondary seed culture was inoculated into a 5 liter fermentor containing 2 liters of a growth medium for fed-batch fermentation, and cultured under conditions of 34° C., pH 6.8, 400 rpm and aeration of 5 l/minute (at atmosphere pressure). When the bacterial growth resulted in glucose concentration of the medium to reach 0.1 g/l, and a constant specific growth rate was maintained at 0.4, a growth limiting substrate (Table 2) was successively added to the fermentor via a peristaltic pump so as to maintain the glucose concentration in the fermentor at 0.1 g/l. When the OD of the bacteria reached to 45 at 580 nm, the temperature of the fermentation medium was raised to 42° C. and the addition medium (Table 3) was added at once to induce the expression while continuing the growth (FIG. 4). The final optical density of the fermentation broth, dry cell weight, the total amounts of protein, the amounts of proinsulin fusion protein produced, the amount of proinsulin produced, and the expression ratio when the growth of the bacteria was ceased, are shown in Table 5.

It could be seen that the amounts of proinsulin fusion protein and proinsulin produced by *E. coli* having pYD21 were 4.76 g/l and 3.97 g/l, respectively and were significantly increased by the fed-batch fermentation, while the amounts of proinsulin fusion protein and proinsulin produced by *E. coli* having pYK10-9, were 2.70 g/l and 2.25 g/l, respectively, which were rather lower than those of the pYD21. Further, in the pYD21, the OD of the final cells was 55 and the expression ratio was 28%. Also, dry cell weight of pYD21 was 37.4 g/l which is less than that of pYK10-9, 75 g/l. Thus, it was confirmed that the pYD21 can contribute to cell disruption and purification procedures. The results of fed-batch fermentation of *E. coli* pop2136 having pYK10-9 and pYD21 are set forth in Table 6 below.

As can be seen from Table 6, the pYD21 which is regulated by an independent expression machinery was more advantageous in many aspects than any other vectors hitherto known.

TABLE 6

Comparison of fed-batch fermentation results of *E. coli* pop 2136/pYK10-9 and pop2136/pYD21

| Item | *E. coli* pop2136 | |
|---|---|---|
| | pYD21 | pYK10-9 |
| Optical density upon expression (580 nm) | 45 | 45 |
| Final optical density after fermentation | 55 | 110 |
| Dry cell weight (DCW) (g/l) | 37.4 | 75 |
| Total amount of protein | 17 | 14 |
| Amount of proinsulin fusion protein (mg/l) | 4760 | 2520 |
| Amount of proinsulin produced (mg/l)*[1] | 3794 | 2104 |
| Expression ratio (%)*[2] | 28 | 18 |

Note)
*[1]Amounts of proinsulin produced (mg/l) = amounts of fusion protein × number of amino acids of proinsulin/number of amino acids of fusion protein.

*[2]Expression ratio (%) = 100 × [amounts of fusion protein produced/total amounts of protein].

Although the invention has been illustrated by way of the above examples, it should be noted that the examples are presented for illustrative purpose only and should not be construed as limiting the invention which is properly delineated in the claims.

What is claimed is:

1. A process for producing human proinsulin in *E. coli* on a large scale comprising the steps of:
   a) inserting a DNA sequence comprising a lac ribosome binding site, a DNA encoding an 11 amino acid leader peptide sequence comprising $(Thr)_6$, and a cDNA encoding human proinsulin, into a plasmid comprising a lambda $P_R$ promotor and a fd phage transcription terminator to construct an expression vector, wherein said cDNA encoding human proinsulin is inserted between said DNA encoding an 11 amino acid leader peptide sequence and said fd phage transcription terminator;
   b) isolating a DNA expression cassette comprising, in turn, a lambda $P_R$ promoter, a lac ribosome binding site, a DNA encoding an 11 amino acid leader peptide sequence comprising $(Thr)_6$, a cDNA encoding human proinsulin, and a fd phage transcription terminator from said expression vector constructed in Step a);
   c) reinserting said DNA expression cassette isolated from Step b) into another said expression vector constructed in Step a) so that the two expression cassettes are transcribed in opposite directions, resulting in an expression vector having two copies of said DNA expression cassettes;
   d) transforming *E. coli* with said expression vector having two copies of said DNA expression cassettes obtained in Step c) to produce a transformant;
   c) culturing said transformant in an appropriate medium; and
   e) recovering said human proinsulin fusion protein.

2. The process according to claim 1 wherein said expression vector is pYD21.

3. The process according to claim 1 wherein said transformant is *E. coli* pop2136/PYD21.

4. The *E. coli* expression vector, PYD21.

5. *E. coli* pop 2136/PYD21.

6. An expression vector for producing human proinsulin in *E. coli* on a large scale comprising two expression cassettes in opposite transcriptional orientations, each expression cassette comprising, in turn, a lambda $P_R$ promoter, a lac ribosome binding site, a DNA encoding an 11 amino acid leader peptide sequence comprising $(Thr)_6$, a CDNA encoding human proinsulin, and a fd phage transcription terminator.

7. A process for producing human proinsulin in *E. coli* on a large scale comprising the steps of:
   a) transforming *E. coli* with an expression vector comprising two expression cassettes in opposite transcriptional orientations, each expression cassette comprising, in turn, a lambda $P_R$ promoter, a lac ribosome binding site, a DNA encoding an 11 amino acid leader peptide sequence comprising $(Thr)_6$, a cDNA encoding human proinsulin, and a fd phage transcription terminator, to produce a transformant;
   b) culturing said transformant in an appropriate medium to produce human fusion protein; and
   c) recovering said human proinsulin fusion protein.

\* \* \* \* \*